US006655214B2

United States Patent
Goodman et al.

(10) Patent No.: US 6,655,214 B2
(45) Date of Patent: Dec. 2, 2003

(54) ULTRASONIC SENSOR HAVING ENHANCED DYNAMIC RANGE

(75) Inventors: Mark A. Goodman, Cortlandt, NY (US); William Bishop, Pleasantville, NY (US)

(73) Assignee: U-E Systems, Inc., Elmsford, NY (US)

( * ) Notice: Subject to any disclaimer, the term of this patent is extended or adjusted under 35 U.S.C. 154(b) by 70 days.

(21) Appl. No.: 10/005,479

(22) Filed: Nov. 12, 2001

(65) Prior Publication Data

US 2003/0089173 A1 May 15, 2003

(51) Int. Cl.⁷ .............................................. G01N 29/00
(52) U.S. Cl. .......................................... 73/649; 73/659
(58) Field of Search .......................... 73/649, 661, 657, 73/592, 593, 660, 587, 405 A; 340/605, 507; 367/135

(56) References Cited

U.S. PATENT DOCUMENTS

| | | | | |
|---|---|---|---|---|
| 4,416,145 A | * | 11/1983 | Goodman et al. ........ 73/40.5 A |
| 4,635,042 A | * | 1/1987 | Andrews ..................... 340/605 |
| 4,785,659 A | * | 11/1988 | Rose et al. ............... 73/40.5 A |
| 4,800,512 A | * | 1/1989 | Busch ........................ 702/182 |
| 4,823,600 A | * | 4/1989 | Biegel et al. ................. 73/592 |
| 4,987,769 A | * | 1/1991 | Peacock et al. .............. 73/49.7 |
| 4,998,439 A | * | 3/1991 | Shepard ........................ 73/592 |
| 5,080,195 A | * | 1/1992 | Mizumoto et al. ........... 184/6.4 |
| 5,089,997 A | * | 2/1992 | Pecukonis ................... 367/135 |
| 5,140,858 A | * | 8/1992 | Nishimoto et al. ............ 73/587 |
| 5,350,040 A | * | 9/1994 | Gribble .................... 184/105.2 |
| 5,432,755 A | * | 7/1995 | Komninos ................... 367/135 |
| 5,691,707 A | * | 11/1997 | Smith et al. ................. 340/682 |
| 5,955,670 A | | 9/1999 | Goodman et al. ............. 73/592 |
| 6,122,966 A | | 9/2000 | Goodman et al. ............. 73/593 |
| 6,339,961 B1 | | 1/2002 | Goodman et al. ............. 73/593 |

* cited by examiner

*Primary Examiner*—Helen Kwok
*Assistant Examiner*—Jacques Saint-Surin
(74) *Attorney, Agent, or Firm*—Darby & Darby (57) ABSTRACT

An externally-powerable sensor is described for detecting ultrasonic energy and for providing an accurate indication of the level of such energy to an external monitoring device over a wide dynamic range. A first electrical signal proportional to the detected ultrasonic energy is chopped by the output of a free-running multivibrator to generate a signal having a frequency differing from the frequency of the first signal by an amount within the audio frequency range. Such difference signal is selectively amplified to concentrate the spectral energy of the difference component in a lower portion of the audio range. A low pass filter extracts, from the so-concentrated difference signal, a modified audio signal whose frequency content is at the lower end, illustratively 0–6 KHz, of the spectrum of the concentrated difference signal. The output of the low pass filter is processed to generate a DC output current that is proportional to the detected ultrasonic energy level. The sensor is connectable to a 4–20 mA current loop which serves to power the sensor electronics as well as to carry the DC output current to the monitoring device.

22 Claims, 5 Drawing Sheets

ULTRASONIC SENSOR HAVING ENHANCED DYNAMIC RANGE

BACKGROUND OF THE INVENTION

The invention pertains to ultrasonic sensors and more specifically to ultrasonic sensors having signal processing subassemblies that may be remotely powered.

An ultrasonic sensor, which typically utilizes a transducer that produces an electrical output in response to received ultrasonic energy, is used to locate and measure leaks or defects in pipes and the like as well as to detect excess friction within mechanical devices. The transducer output is coupled to a signal processing subassembly that derives a measurement signal proportional to the transducer output. The measured ultrasonic energy is generally in the range of 20–100 KHz, which is too high in frequency to be heard by a human being. Thus, the signal processing subassembly is sometimes adapted to frequency shift the detected signal into the 0–20 Khz audio range. In some cases, the subassembly includes facilities for deriving monitoring a DC signal proportional to such audio signal.

Because of the low levels of the ultrasonic signals detected by a sensor of this type, it has been necessary to augment the detected signal using a high-gain preamplifier before it can be further processed. In order to prevent such amplified signal from saturating the heterodyne and measurement circuitry, it has been common to attenuate the preamplified signal. Unfortunately, with such arrangements the maximum device sensitivity—i.e., the dynamic range of ultrasonic signal inputs that can be accurately processed by the sensor—has been limited typically to the range of 30–40 DB.

SUMMARY OF THE INVENTION

Such limitations on dynamic range are minimized with an ultrasonic sensor in accordance with the invention. In an illustrative embodiment, the preamplified output of an ultrasonic transducer is chopped by the output of a free-running oscillator which generates a selectable frequency differing from the frequency of the transducer output by an amount within the audio frequency range. The output of the chopper includes a signal having a frequency equal to the difference of the frequencies of the transducer and the oscillator.

The frequency components of such difference signal are selectively amplified to concentrate the spectral energy of the difference signal in a lower portion of the audio range. A low pass filter extracts, from the so-concentrated difference signal, a modified audio signal whose frequency content is at the lower end, illustratively 0–6 KHz, of the spectrum of the concentrated difference signal.

Preferably, the output of the low pass filter is coupled to an AC to DC converter which provides a DC voltage that is proportional to the ultrasonic energy level detected by the transducer. As an additional feature of the invention, the AC to DC converter utilizes a compression network that prevents the converter output from saturating over the enhanced dynamic range of the input signal.

The improved sensitivity provided by the arrangement of the invention allows the sensor to be employed effectively with an external power supply. Illustratively, the sensor is connected to a 4–20 mA current loop which may serve both as a vehicle for powering of the signal processing subassembly of the sensor as well as for carrying an output current proportional to the DC voltage generated by the sensor. Such current may be generated by a suitable voltage to current converter in the signal processing subassembly of the sensor.

BRIEF DESCRIPTION OF THE DRAWING

These and other aspects, features and advantages of the invention are further set forth in the following detailed description of an illustrative embodiment thereof taken in conjunction with the appended drawing, in which.

DETAILED DESCRIPTION

Figure 1:
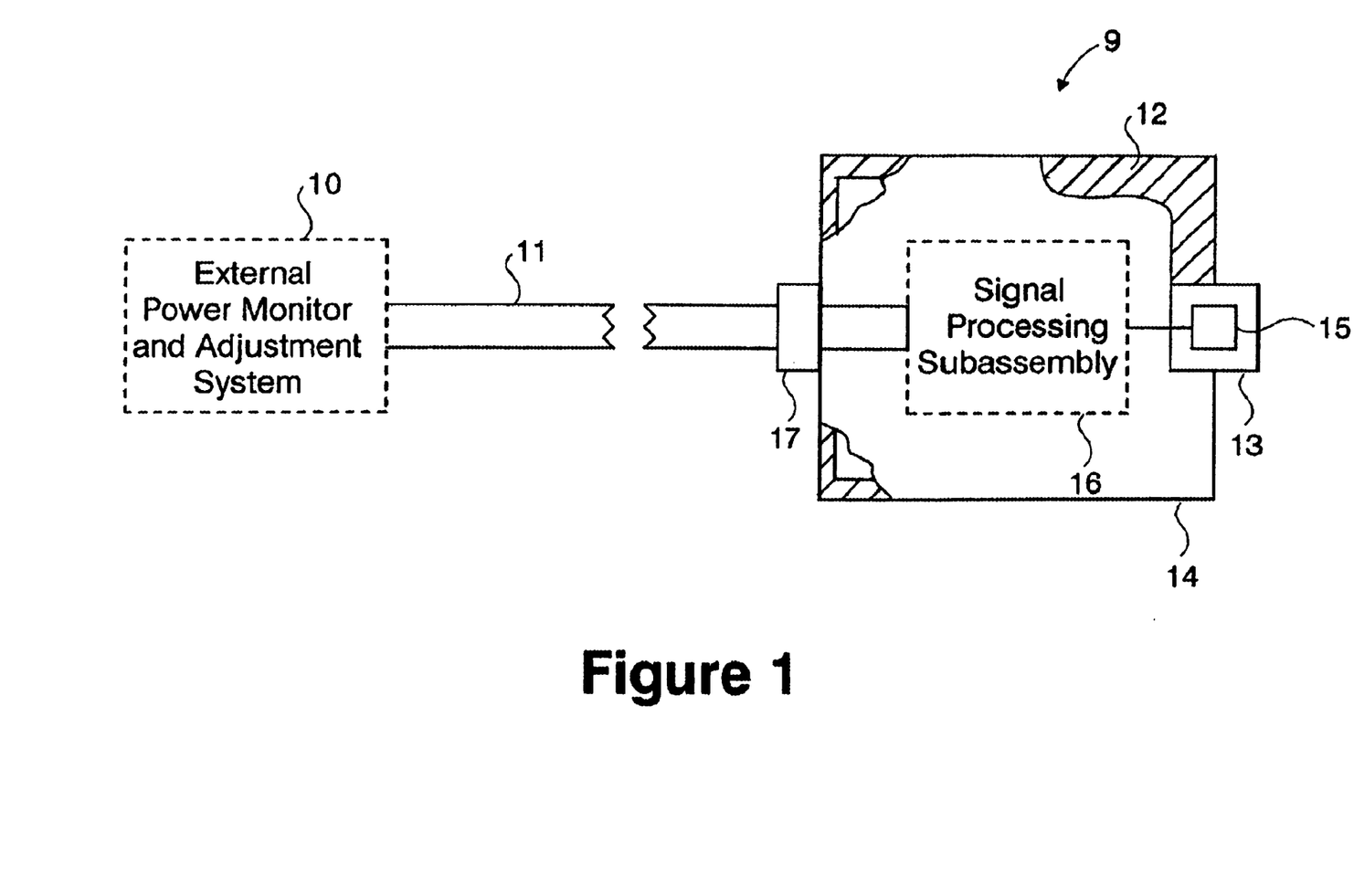
FIG. 1 is a pictorial representation of an externally powerable ultrasonic sensor that is adapted for enhanced measurement sensitivity in accordance with the invention.

Referring to the drawing, FIG. 1 shows an illustrative embodiment of an ultrasonic sensor 9 which may be remotely powered, monitored and adjusted from a suitable external system 10 through an I/O cable 11. The sensor 9 includes a hollow moisture-resistant housing 12 formed from a conductive material. A transducer mount 13 is secured in one end 14 of the housing 12, and supports a conventional ultrasonic transducer 15 that assumed to be formed from a single piezoelectric crystal.

The transducer 15 may be coupled in a conventional manner through the mount 13 to a workpiece (not shown) which is to be measured ultrasonically for flaws, defects, excess friction or the like. The transducer 15 is conventionally operable to convert measured ultrasonic oscillations in a frequency range of 20–100 KHz into a corresponding electrical signal. The transducer 16 may be arranged to detect either structure-borne or acoustic ultrasonic signals in a conventional manner. The electrical signal at the output of the transducer 15 is coupled to the input of a signal processing subassembly 16 located in the interior of the housing 12.

Figure 2:
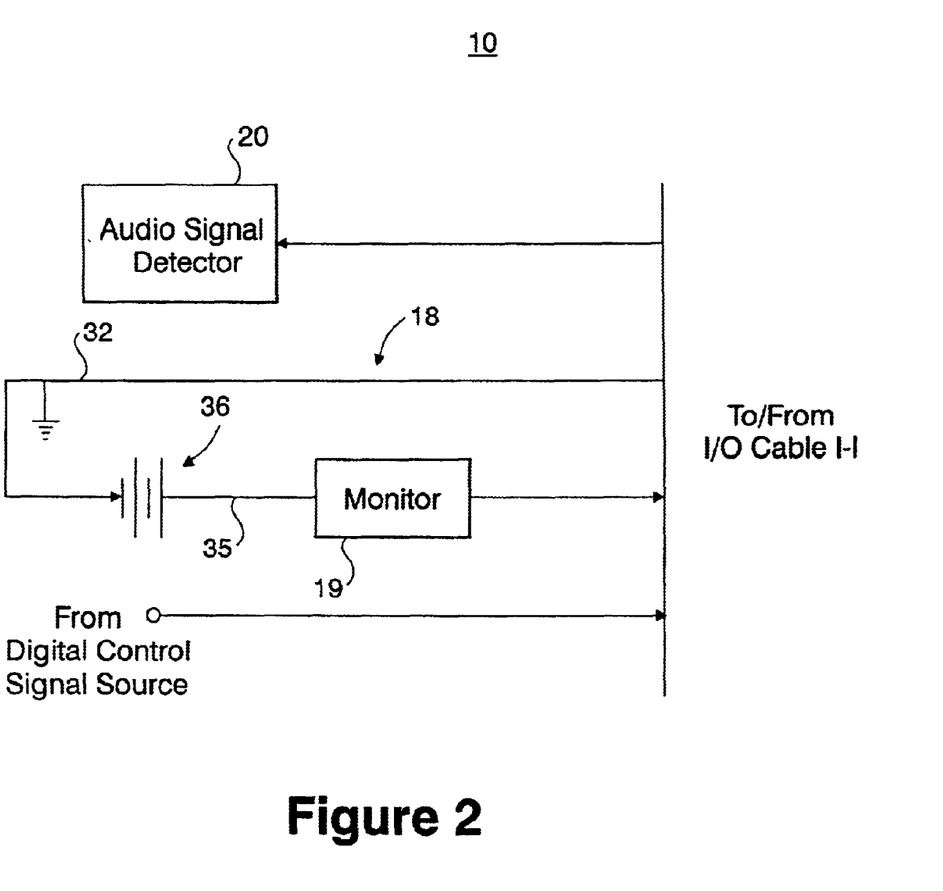
FIG. 2 is a representation of external facilities for powering, controlling, and monitoring measurement signals from the sensor of FIG. 1.

The I/O cable 11 is directly connected to the subassembly 16 through the housing 12 via a moisture resistant cable fitting 17 for applying power to the subassembly from an external current loop 18 (FIG. 2). Such current loop, which is illustratively a 4–20 mA current loop, forms part of the system 10. Advantageously, the cable 11 may also be adapted to provide digital control signals from the system 10 for remotely adjusting parameter(s), such as the sensitivity and/or carrier frequency, of the subassembly 16 (FIG. 1)

As indicated below, the subassembly 16 is adapted to generate a first DC output signal and a second audio output signal each proportional to the transducer output signal. Such DC and audio output signals are respectively coupled through the I/O cable 11 to a monitor 19 (FIG. 2) in the current loop 18 and to a suitable audio detector 20 in the external system 10.

Figure 3:
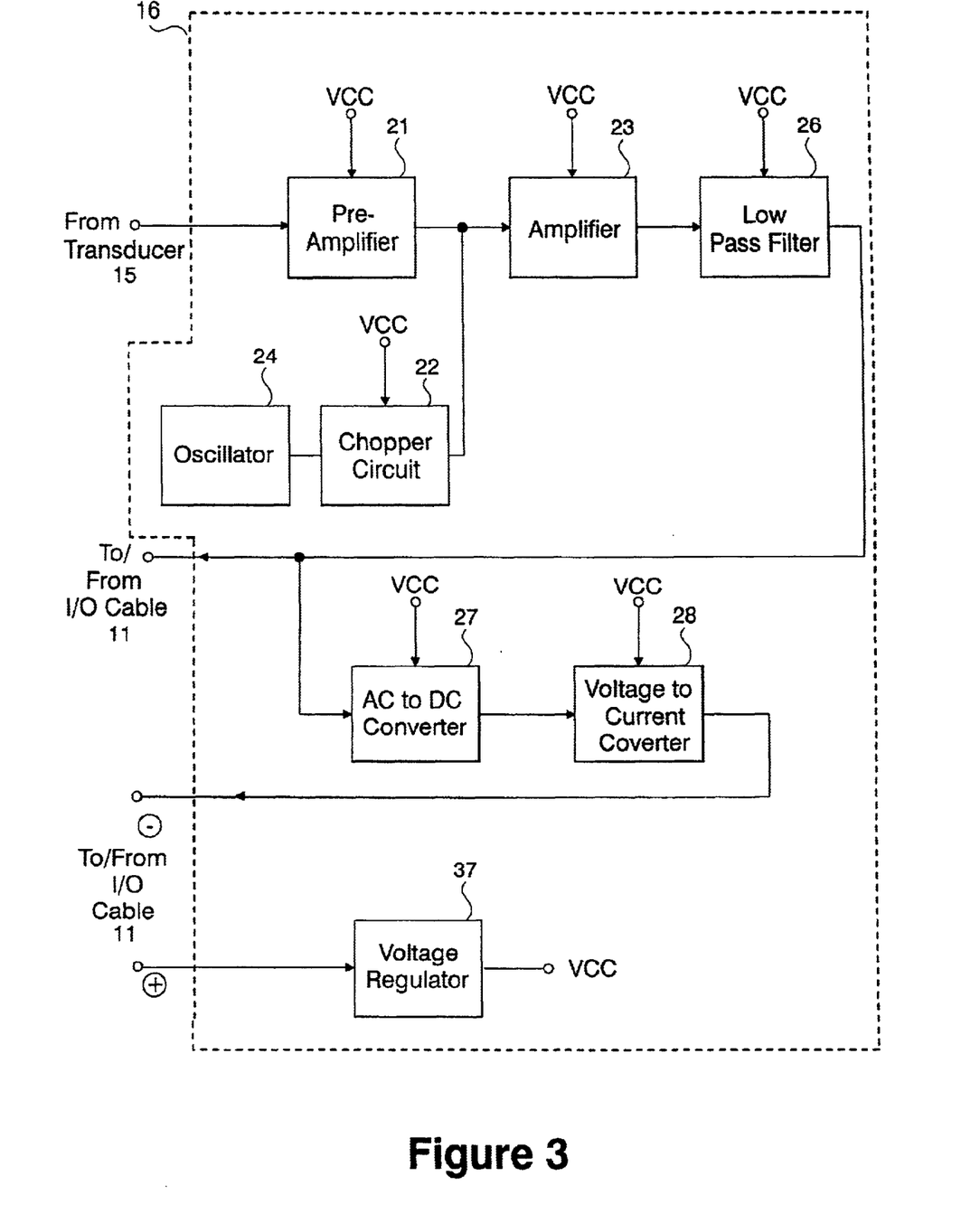
FIG. 3 is a block diagram of the signal processing subassembly in the sensor of FIG. 2.

As shown in FIG. 3, the subassembly 16 includes a preamplifier 21 to which the 20–100 KHz electrical signal from the transducer 15 is applied. The resultant amplified signal is then subjected to a heterodyne mode where it is effectively frequency-shifted into the audio range. This operation may be illustratively implemented in an optimum manner by chopping the output of the preamplifier 21 with a chopper circuit 22 in the manner indicated below, and applying the chopped signal to the input of a high gain linear amplifier 23. The chopper circuit 22 operates at a rate governed by an adjustable-frequency oscillator 24. The chopped signal has a frequency spectrum with components representing the sum of, and the difference between, the frequency at the output of the transducer 15 and the carrier frequency at the output of the oscillator 24. The carrier frequency is adjusted so that the difference component is in the audio frequency range.

The oscillator 24 is illustratively tuned to a carrier frequency in the 30–50 KHz range (e.g., 37 KHz), although adjustability over other suitable ranges, such as 20–100 KHz, may also be used. Such expanded range may be particularly appropriate when the ultrasonic energy being measured is at the high end of the 20–100 KHz range to assure that the difference component at the output of the chopper 22 is within the audio range.

The gain of the linear amplifier 23 is preferably more pronounced at the lower end of the frequency range of the incoming chopped signal, so that the spectrum of the difference component, and in particular a lower portion of such spectrum, will be augmented. Such selective augmentation of the difference component serves to concentrate the spectral energy of the difference component in a band significantly below the 20 KHz band typically appearing at the audio output of previous ultrasonic sensors.

A low pass filter 26 at the output of the linear amplifier 23 eliminates any residual sum frequency components resulting from the action of the chopper circuit 22 and further narrows the band of the concentrated difference component from the amplifier 23 to a range of about 0–6 KHz. The resultant output of the filter 26 is proportional to the ultrasonic energy detected by the transducer 15.

The audio output from the filter 26 is coupled to the I/O cable 11 for application to the audio detector 20 (FIG. 2), which may be associated with a suitable utilization device such as a spectrum analyzer (not shown). The output of the filter 26 (FIG. 4A) is also applied to the input of an AC-DC converter 27. The DC output of the converter 27 is proportional to the detected ultrasonic signal level of the transducer 15. Such DC voltage is applied to a voltage to current converter 28 which generates a DC output current proportional to the detected ultrasonic signal level.

Such DC output current is connected, through the ground conductor (not shown) of the I/O cable 11 and a grounded negative lead 32 (FIG. 2) of the current loop 18, to a fixed DC supply 36 disposed in the loop 18. The monitor 19 is connected to a positive lead 35 of the loop 18. Voltage from the supply 36 is applied, through the positive lead 35 and the positive power conductor (not shown) of the I/O cable 11, to a conventional voltage regulator 37 (FIG. 3) in the signal processing subassembly 16. The voltage regulator 37 derives a regulated positive voltage, designated VCC, necessary to power the components of the subassembly 16. Illustratively, VCC is 10 volts.

Figure 4A:
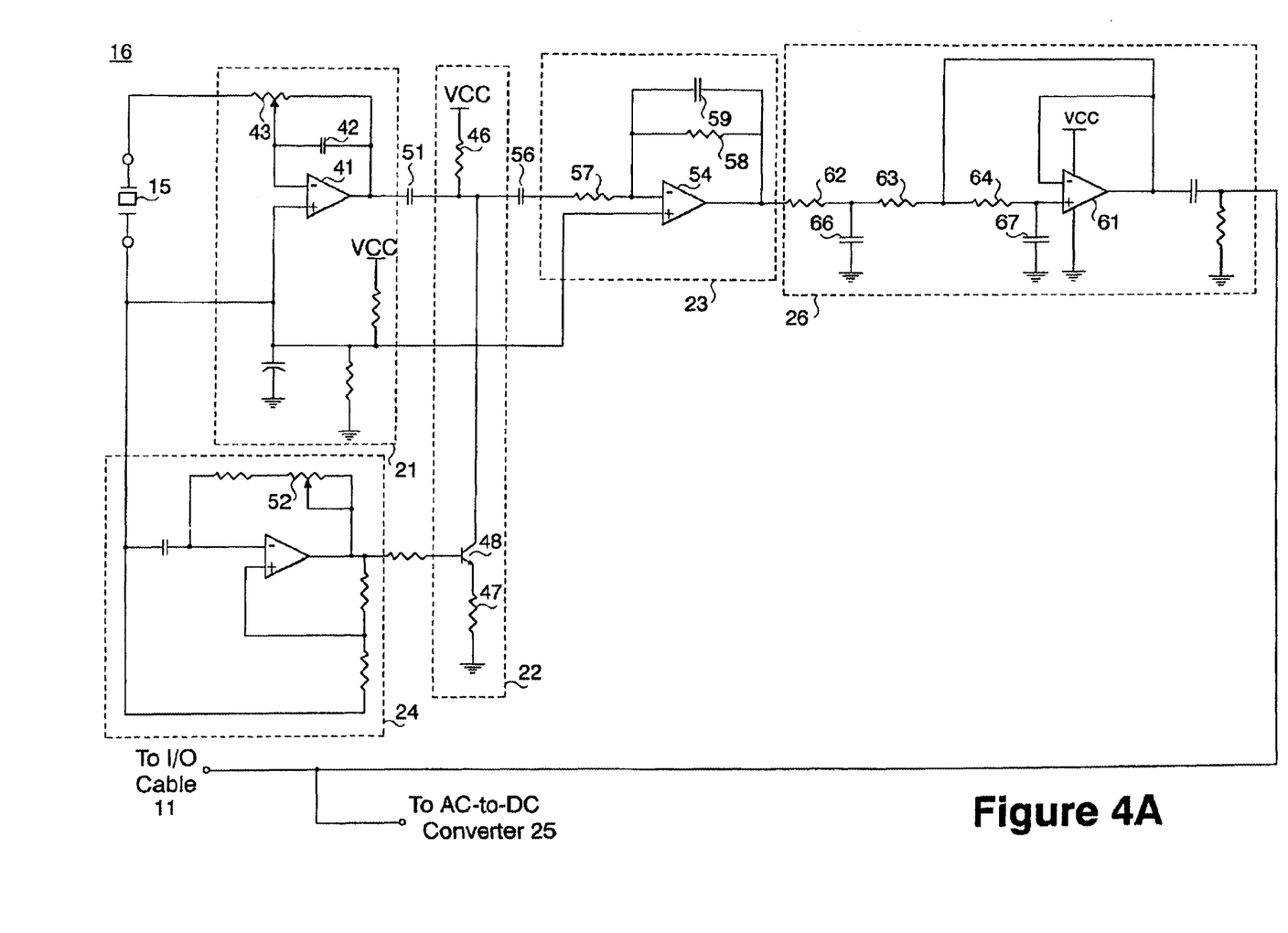
FIGS. 4A and 4B are schematic diagrams of the components of the signal processing subassembly of FIG. 3.
Figure 4B:
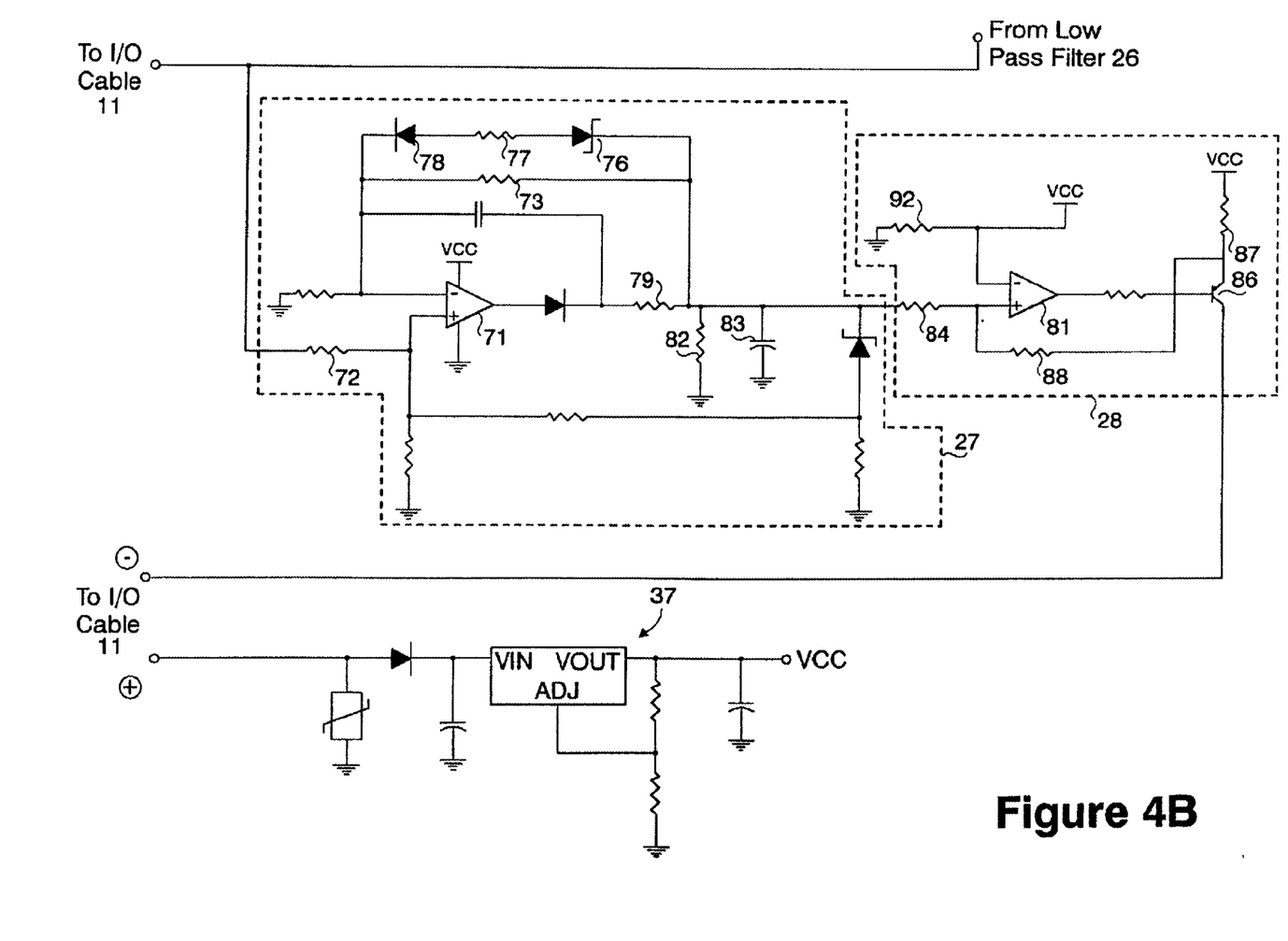

FIGS. 4A and 4B depict an illustrative circuit arrangement for the components of the subassembly 16. The preamplifier 21, whose maximum gain may typically be 100 DB or greater, conventionally includes an operational amplifier 41 having a parallel RC negative feedback loop having a capacitor 42 and a variable resistor 43. The non-inverting input of the amplifier 41 is biased to one half of the supply voltage VCC. When the resistor 43 is adjusted to present maximum resistance in the feedback loop, the amplifier 41 operates as a charge amplifier wherein the 20–100 KHz output voltage from the transducer 15 is coupled directly to the inverting input of the amplifier 41. For other settings of the resistor 43, the amplifier 41 acts as a conventional voltage amplifier.

As indicated above, the spectrum of the amplified 20–100 KHz signal at the output of the preamplifier 21 is altered by the chopper circuit 22. Illustratively, the chopper circuit 22 includes a voltage divider utilizing a pair of resistors 46 and 47 and the collector-emitter path of a transistor 48 that are connected in series between VCC and ground. The output signal from the preamplifier 21 is coupled, through a capacitor 51, to the junction of the resistor 46 and the collector of the transistor 48. The base of the transistor 48 is coupled to the output of the oscillator 24, which may be conventionally embodied as a free-running multivibrator. The selection of the carrier frequency of the oscillator 24 is implemented by adjustment of a variable resistor 52. Advantageously, such adjustment may be remotely accomplished by digital control signals from the system 10 (FIG. 2), in which case the variable resistor 52 may be embodied in programmable digital form. In an appropriate case, the variable resistor 52 may be shunted with an auxiliary resistor (not shown) to raise the carrier frequency by an amount sufficient to help assure that the difference frequency component at the output of the chopper circuit 22 is in the audio range as indicated above.

The chopper circuit 22 is so configured that the resistance of the resistor 46 is much greater than that of the resistor 47. Under the circumstances, the 20–100 KHz output of the preamplifier 21 is chopped by being periodically driven essentially to ground when the transistor 48 conducts. Such chopping action occurs at the carrier frequency of the oscillator 24.

The components of the chopped signal are applied through a capacitor 56 and a resistor 57 to the high gain linear amplifier 23, which is illustratively embodied as an inverting operational amplifier 54. The amplifier 54 has a parallel RC negative feed back loop including a resistor 58 and a capacitor 59. The value of the resistor 58 (illustratively 470K ohms) is advantageously made about 50 times greater than that of the resistor 57.

The difference component of the chopped signal is concentrated by the amplifier 23 to enhance the spectral energy of such difference component at frequencies well below 20 KHz. Such enhancement results from the high nominal amplification (e.g., 20–30 DB) presented by the amplifier 23 and, preferably, by selectively reducing the gain presented to the higher audio frequencies of the difference component. For this purpose the value of the feedback capacitor 59 is made relatively large, for example 470 pF. Such large capacitance also serves suppress the sum components of the chopped signal.

The so-concentrated difference signal from the linear amplifier 23 is applied to the input of the low pass filter 26, illustratively a third order low pass filter that is embodied using an operational amplifier 61, resistors 62, 63 and 64 and capacitors 66 and 67. The values of such resistors and capacitors are chosen such that the 3 DB break point for the filter 26 occurs at about 6 KHz. The resulting 0–6 KHz audio signal at the output of the filter 26 has an amplitude proportional to the measured ultrasonic energy at the transducer 15, and is applied both to the AC to DC converter 27 and to the I/O cable 11.

The converter 27, which is illustratively a full-wave rectifier, includes a operational amplifier 71 (FIG. 4B). The audio output from the filter 26 is applied through a resistor 72 to the non-inverting input of the amplifier 71. A feedback path extends from the output of the amplifier 71 to the inverting input thereof, and operates as a compression network. Specifically, such feedback path has a first branch that includes a resistor 73, and a second parallel branch including a zener diode 76 in series with a resistor 77 and a diode 78. With this arrangement, when the audio input voltage to the converter 27 rises above a threshold value that causes the voltage across an output resistor 79 to trigger on the zener diode 76, the gain of the amplifier 71 will be reduced to prevent saturation at the output of the converter 27. Because of the action of the compression network just described, the effective dynamic range of the converter 27 may be increased by up to 15 DB.

The voltage to current converter 28 illustratively includes an operational amplifier 81. The output of the AC to DC converter 27, generated across a parallel RC path including a resistor 82 and a capacitor 83, is applied to the non-inverting input of the amplifier 81 through a resistor 84. The output of the amplifier 81 is coupled to the base of a transistor 86, whose collector-emitter path is connected to a load resistor 87 and through a resistor 88 to the non-inverting input of the amplifier 81. The inverting input of the amplifier 81 is biased from a voltage divider consisting of resistors 91 and 92 connected in series between VCC and ground. With this arrangement, the current through the load resistor 87 is proportional to the DC input voltage to the amplifier 81. Such current constitutes a DC indication proportional to the ultrasonic energy to be externally monitored in the external current loop 18 (FIG. 2).

A principal advantage of the arrangement of the invention just described is that the sensitivity of ultrasonic measurement is significantly greater than that of prior art ultrasonic sensor arrangements. This effect is particularly evident in the case where the sensor 9 is powered with the 4–20 mA current loop 18 as indicated above. Using such loop, the sensor gain setting is first initialized by adjustment of the variable resistor 43 (FIG. 4A) so that the current at the collector of the transistor 86 (FIG. 4B) of the voltage to current converter 28 is 4 mA when a minimal ultrasonic level is detected. Such adjustment is advantageously done remotely by means of digital control signals from the external system 10 (FIG. 2), in which case the variable resistor 43 (FIG. 4A) may be embodied in programmable digital form. Once such adjustment is done, the spread between maximum and minimum values of the measured output current from the converter 28 (FIG. 4B) during a working measurement corresponds typically to a 50 DB dynamic range of the detected ultrasonic energy.

In the foregoing, the invention has been described in connection with a preferred arrangement thereof. Many variations and modifications will now occur to those skilled in the art. For example, while for purposes of illustration the DC output quantity from the subassembly 15 has been described as a current proportional to the detected ultrasonic signal, such quantity may also be a DC voltage obtained by substituting a voltage amplifier for the voltage to current converter 28. In such case, the 50 DB dynamic range of the sensor 9 (FIG. 1) may be represented by various output voltage ranges, typically 0–5 or 0–10 volts. It is accordingly desired that the scope of the appended claims not be limited to or by the specific disclosure herein contained.

What is claimed is:

1. In a detector for sensing energy in the ultrasonic frequency range:
    a transducer responsive to ultrasonic energy incident thereon for generating a first electrical signal that is related to the intensity and frequency of the ultrasonic energy;
    an oscillator having a selectable frequency of operation for generating a second electrical signal differing from the frequency of the first signal by an amount within an audio frequency range;
    a heterodyning stage responsive to the first and second signals for generating a third electrical signal having a frequency equal to a difference of the frequencies of the first and second signals; and
    a first amplifier coupled to the output of the heterodyning stage for concentrating the spectral energy of the third signal in a lower portion of the audio frequency range.

2. A detector as defined in claim 1, wherein the first amplifier comprises means for reducing the gain presented by the first amplifier to higher frequency components of the spectrum of the third signal.

3. A detector as defined in claim 1, wherein the heterodyning stage comprises a device for chopping the first signal with the second signal.

4. In a detector for sensing energy in the ultrasonic frequency range:
    a transducer responsive to ultrasonic energy incident thereon for generating a first electrical signal that is related to the intensity and frequency of the ultrasonic energy;
    an oscillator having a selectable frequency of operation for generating a second electrical signal differing from the frequency of the first signal by an amount within an audio frequency range;
    a heterodyning stage responsive to the first and second signals for generating a third electrical signal having a frequency equal to a difference of the frequencies of the first and second signals; and
    an amplifier for amplifying the third signal, the amplifier including means for reducing the gain presented to higher frequency components of the third signal to concentrate the spectral energy of the third signal in a lower portion of the audio frequency range.

5. A detector as defined in claim 4, wherein the heterodyning stage comprises a device for chopping the first signal with the second signal.

6. In a detector for sensing energy in the ultrasonic frequency range:
    a transducer responsive to ultrasonic energy incident thereon for generating a first electrical signal that is related to the intensity and frequency of the ultrasonic energy;
    an oscillator having a selectable frequency of operation for generating a second electrical signal differing from the frequency of the first signal by an amount within an audio frequency range;
    a first device for chopping the first signal with the output of the oscillator to generate a third electrical signal having a frequency equal to a difference of the frequencies of the first and second signals;
    an amplifier coupled to the output of the first device for concentrating the spectral energy of the third signal in a lower portion of the audio range; and
    a low pass filter coupled to the output of the first device for extracting a fourth signal exhibiting a lower portion of the spectrum of the so-concentrated third signal.

7. A detector as defined in claim 6, wherein the first device comprises means for reducing the gain presented by the first amplifier to higher frequency components of the spectrum of the third signal.

8. In a detector for sensing energy in the ultrasonic frequency range:

a transducer responsive to ultrasonic energy incident thereon for generating a first electrical signal that is related to the intensity and frequency of the ultrasonic energy;

an oscillator having a selectable frequency of operation for generating a second electrical signal differing from the frequency of the first signal by an amount within an audio frequency range;

a heterodyning stage responsive to the first and second signals for generating a third electrical signal having a frequency equal to a difference of the frequencies of the first and second signals;

an amplifier for amplifying the third signal, the amplifier including a device for reducing the gain presented to higher frequency components of the third signal to concentrate the spectral energy of the third signal in a lower portion of the audio frequency range; and a low pass filter coupled to the output of the amplifier for extracting a fourth signal exhibiting a lower portion of the spectrum of the concentrated third signal.

9. A detector as defined in claim 8, wherein the heterodyning stage comprises a device for chopping the first signal with the second signal.

10. A detector for sensing energy in the ultrasonic frequency range and for providing an indication of the level of such energy at an external monitoring device, which comprises:

a transducer responsive to ultrasonic energy incident thereon for generating a first electrical signal that is related to the intensity and frequency of the ultrasonic energy;

an oscillator having a selectable frequency of operation for generating a second electrical signal differing from the frequency of the first signal by an amount within an audio frequency range;

a heterodyning stage responsive to the first and second signals for generating a third electrical signal having a frequency equal to a difference of the frequencies of the first and second signals;

a first amplifier coupled to the output of the heterodyning stage for concentrating the spectral energy of the third signal in a lower portion of the audio frequency range;

a low pass filter coupled to the output of the first amplifier for extracting a fourth signal exhibiting a lower portion of the spectrum of the concentrated third signal; and a device for coupling the fourth signal to a monitoring device.

11. A detector for sensing energy in the ultrasonic frequency range and for providing an indication of the level of such energy at an external monitoring device, which comprises:

a transducer responsive to ultrasonic energy incident thereon for generating a first electrical signal that is related to the intensity and frequency of the ultrasonic energy;

an oscillator for generating a second electrical signal having a selectable frequency differing from the frequency of the first signal by an amount within the audio frequency range;

first means responsive to the first and second signals for generating a third electrical signal having a frequency equal to the difference of the frequencies of the first and second signals;

means including a first amplifier coupled to the output of the first generating means for concentrating the spectral energy of the third signal in a lower portion of the audio range;

a low pass filter coupled to the output of the amplifying means for extracting a fourth signal exhibiting a lower portion of the spectrum of the concentrated third signal;

second means having a first input coupled to the low pass filter for generating a first DC quantity having a level related to the amplitude of the fourth signal; and means for coupling the first DC quantity to the monitoring device.

12. A detector as defined in claim 11, in which the first generating means comprises means for chopping the first signal with the second signal.

13. A detector as defined in claim 11, in which the concentrating means comprises means for reducing the gain presented by the first amplifier to higher frequency components of the spectrum of the third signal.

14. A detector as defined in claim 11, in which the oscillator is a free-running multivibrator.

15. A detector as defined in claim 11, in which the second generating means comprises an AC to DC converter.

16. A detector as defined in claim 15, in which the AC to DC converter comprises, in combination, a second amplifier, and means for reducing the gain of the second amplifier when the amplitude of the fourth signal exceeds a predetermined value.

17. A detector as defined in claim 16, in which the gain reducing means comprises a negative feedback path extending from the output of the second amplifier to a first input thereof, the feedback path comprising, in combination, a first branch having a first impedance, a second branch having a second impedance, normally inoperative switching means for connecting the second branch across the first branch, and means responsive when the amplitude of the fourth signal exceeds the predetermined value for operating the switching means.

18. A detector as defined in claim 17, in which the switching means comprises a zener diode.

19. A detector as defined in claim 11, in which the first quantity is a DC current, and in which the second generating means comprises, in combination, an AC to DC converter coupled to the output of the low pass filter, and a voltage to current converter coupled to the output of the AC to DC converter.

20. A detector as defined in claim 11, in which the monitoring device is coupled to an external voltage source, and in which the coupling means is connectable in a common current loop with the monitoring device and the external voltage source.

21. A detector as defined in claim 20, further comprising means coupled to the external voltage source through the common current loop for generating a regulated voltage supply.

22. A detector for sensing energy in the ultrasonic frequency range and for providing an indication of the level of such energy to first and second external measuring devices, which comprises:

a transducer responsive to ultrasonic energy incident thereon for generating a first electrical signal that is related to the intensity and frequency of the ultrasonic energy;

an oscillator for generating a second electrical signal having a selectable frequency differing from the frequency of the first signal by an amount within the audio frequency range;

first means responsive to the first and second signals for generating a third electrical signal having a frequency equal to the difference of the frequencies of the first and second signals;

means including a first amplifier coupled to the output of the first generating means for concentrating the spectral energy of the third signal in a lower portion of the audio range;

a low pass filter coupled to the output of the amplifying means for extracting a fourth signal exhibiting a lower portion of the spectrum of the concentrated third signal;

means for coupling the fourth signal to the first measuring device;

second means having a first input coupled to the low pass filter for generating a DC quantity having a level related to the amplitude of the fourth signal; and means for coupling the DC quantity to the second measuring device.

* * * * *